(12) United States Patent
Bonne et al.

(10) Patent No.: US 6,792,794 B2
(45) Date of Patent: Sep. 21, 2004

(54) LOW POWER GAS LEAK DETECTOR

(75) Inventors: Ulrich Bonne, Hopkins, MN (US); Paul Bauhahn, Fridley, MN (US); Claudio C. Groppetti, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/350,234

(22) Filed: Jan. 23, 2003

(65) Prior Publication Data

US 2004/0060346 A1 Apr. 1, 2004

Related U.S. Application Data

(60) Provisional application No. 60/414,211, filed on Sep. 27, 2002.

(51) Int. Cl.[7] .............................................. G01N 25/00
(52) U.S. Cl. .................... 73/25.01; 73/25.05; 73/29.05; 73/31.05
(58) Field of Search ................................ 73/23.2, 31.07, 73/24.06, 25.01, 25.05, 29.05, 31.05, 31; 422/88

(56) References Cited

U.S. PATENT DOCUMENTS

| | | | | |
|---|---|---|---|---|
| 4,478,076 A | * | 10/1984 | Bohrer | 73/204.16 |
| 4,576,050 A | * | 3/1986 | Lambert | 73/861.95 |
| 4,759,210 A | * | 7/1988 | Wohltjen | 73/31.07 |
| 4,944,035 A | | 7/1990 | Aagardl et al. | 702/136 |
| 5,852,308 A | * | 12/1998 | Wood | 257/252 |
| 5,869,749 A | * | 2/1999 | Bonne et al. | 73/53.01 |
| 5,889,196 A | * | 3/1999 | Ueno et al. | 73/23.31 |
| 6,393,894 B1 | | 5/2002 | Bonne et al. | 73/23.2 |
| 2002/0124631 A1 | * | 9/2002 | Sunshine et al. | 73/23.2 |

OTHER PUBLICATIONS

Bonne, U., et al., "New Gas Composition and Trace Contaminant Sensors," GTI Natural Gas Technologies Conference, Orland, FL, Sep. 30–Oct. 2, 2002, pp. 1–12.
Cabuz, C., et al., "The Dual Diaphragm Pump," IEEE, pp. 519–522, 2001.
Cabuz, C. et al., "Mesoscopic Sampler Based on 3–DF Arrays of Electrostatically Actuated Diaphragms," Proc. 10th Conf. S.S. S&A. Transducers '99 Jun. 7–12, 1999, Sendai, Japan.
Honeywell Electronic Materials Interconnect Solutions, Thin Films—Dielectrics, Comparison of Solution and Film Properties, Advanced Products for IC Fabrication, 1 page.
Phillips, J.B. et al., "Thermal Modulation: A Chemical Instrumentation Component of Potential Value in Improving Portability," Field Analytical Chemistry and Technology, 1(1): 23–29, 1996.
Kenndler, Ernst, "Gas Chromatography," Institute for Analytical Chemistry, University of Vienna, pp. 1–34, Sep. 9, 1999.
NexTrieve document view, http://www.chrompack.com/cgi/applicsview?ap=A00764, 2 pages.
Stevenson, Robert, "Wintergreen '97," The World of Separation Science, The 19th Internatinal Symposium on Capillary Chromatography and Electrophoresis, 11 pages.

* cited by examiner

Primary Examiner—Hezron Williams
Assistant Examiner—David A Rogers
(74) Attorney, Agent, or Firm—Kris T. Fredrick

(57) ABSTRACT

A leak detector having a multi-stage concentrator, consisting of an array of heater elements which desorb analytes in a phased manner, in synch with the sample stream, to maximize sensitivity. The heater elements of the concentrator are coated with adsorber material on both sides of the heater elements, i.e., top and bottom sides, and have small anchor points to minimize power dissipation. The concentrated gas mixture output of the concentrator is electronically injected into a separator, which for separates the constituents of the detected analyte-fluid and recognizing the nature or source of the analyte.

30 Claims, 13 Drawing Sheets

Table 1. Approximate Power Budget and Thermal Conductance Calculation for the Detector

Assume the total thermal resistance is the thermal resistance of Pt film, in series with the Si3N4 that connects Pt film to Si substrate.
(i.e. neglect thermal conductance of Si3N4 layers above and below the Pt)

|  | Pt | SI3N4 | One Analisis / s Cumulative |  |
|---|---|---|---|---|
| Thermal conductivity: | 7.30E-05 | 1.90E-06 | W /(um K) | |
| Thickness | 0.06 | 1.5 | um | |
| Effective length | 40 | 10 | um | |
| Width: | 5000 | 5000 | um | |
| Thermal resistance: | 1.83E+03 | 7.02E+02 | K/W | |
| Total Thermal resistance: | 2.53E+03 | | K/W | |
| Temperature Difference: | 180 | | K | |
| Power Required (half of device): | 71.20 | | mW | |
| Power Required (whole device): | 142.39 | | mW | |
| Power (Conc. array: 30 el.x 5 ms/ea): | 21.36 | | 21.36 avg. mW for one analysis/s | |
| Power (Sep. array: 30 el.x1s /2): | 1068.00 | | 1089.36 mW for temp.progr to 90K rise | |
| Heat sample stream by 180K | 9.01 | | 1098.37 mW steady for 1 s | |
| Electronics | 100.00 | | 1198.37 mW | |
| Pump | 100.00 | | 1298.37 mW | |
| | | | 1298.37 mW | |
| Energy reductions | | | 1298.37 mW | |
| Redesign Conc.heater elements | -19.22 | | 1279.15 mW | |
| Redesign Sep.heater elements | -961.20 | | 317.95 mW | |
| Low power electr. & pump | -100.00 | | 217.95 mW | |
| One analysis every 3 seconds: | -125.30 | | 92.65 mW average | |

As shown above, energy conservation measures on the sensor may reduce the energy needed per analysis (initiated once every 3 seconds) from about 1.7 Joules and peak power of ~1280 mW, down to about 0.4 Joules, with peak power of 220 mW.

Fig.13

LOW POWER GAS LEAK DETECTOR

This application claims the benefit of U.S. Provisional Application No. 60/414,211, entitled "PHASED SENSOR", filed Sep. 27, 2002, wherein such document is incorporated herein by reference.

BACKGROUND

The invention pertains to detection, identification and analyses of gases. Related art fuel gas leak detectors may be low-cost (and in part reasonably sensitive) but cannot identify the nature of the fuel leak (natural gas, swamp gas, propane or gasoline vapors), while others such as portable GCs (gas chromatographs) are both moderately sensitive and able to identify the fuel, but are very costly, slow (greater than about ten seconds response time) and consume much power.

Aspects of structures and processes related to gas detectors may be disclosed in U.S. Pat. No. 6,393,894, issued May 28, 2002, and entitled "Gas Sensor with Phased Heaters for Increased Sensitivity," which is incorporated herein by reference, and in U.S. Pat. No. 4,944,035, issued Jul. 24, 1990, and entitled "Measurement of Thermal Conductivity and Specific Heat," which is incorporated herein by reference.

SUMMARY

A gas leak detector and analyzer may be realized via affordable, in-situ, ultra-sensitive, low-power, low-maintenance and compact micro detectors and analyzers, which can wirelessly or by another medium (e.g., wire or optical fiber) send their detection and/or analysis results to a central or other manned station. A micro gas leak detector incorporating a phased heater array, concentrator and separator as an enhanced detector contribute to the availability of a low-cost multi-gas analyzer and system to provide gas leak detection.

The present gas leak detector is low-power, fast, compact, low cost, intelligent, wireless or not, low maintenance, robust and highly sensitive. It is a phased heater based leak detector that responds in about one second, uses less than one watt of power, can identify the nature of the fuel via its constituents, and is palm-top-sized and thus very portable The heater elements of a phased heater array may be coated with an adsorber material on both surfaces, i.e., top and bottom sides, for less power dissipation and more efficient heating of the incoming detected gas. The heater elements may have small widths for reduced power dissipation. There is a heater membrane that has a small number anchor points for little heat conduction from the heater elements.

The surfaces of inside channels of the heater array, except those surfaces intentionally by design coated with an adsorber material, may be coated with a non-adsorbing, thermal insulating layer. The thickness of the adsorber coating or film is reduced thereby decreasing the time needed for adsorption and desorption. A thrifty pump may be implemented for pulling in a sample of the fluid being checked for detection of a possible gas leak from somewhere. Low-power electronics having a sleep mode when not in use may be utilized. Thus, the present leak detector uses very little power.

The gas leak detector may be integrated on a chip with conventional semiconductor processes or micro electromechanical machined system (MEMS) techniques. This kind of fabrication results in low-power consumption, compactness and in situ placement of the detector. The flow rate of the air or gas sample through the detector may be very small. Further, a carrier gas for the samples is not needed and thus this lack reduces the dilution of the samples being tested, besides eliminating the associated maintenance and bulk of pressurized gas-tank handling. This approach permits the detector to provide quick analyses and prompt results, maybe at least an order of magnitude faster than some related art devices. It avoids the delay and costs of labor-intensive laboratory analyses. The detector is intelligent in that it may have an integrated microcontroller for analysis and determination of gases detected, and may maintain accuracy, successfully operate and communicate information in and from unattended remote locations. The detector may communicate detector information, analyses and results via utility lines, or optical or wireless media, with the capability of full duplex communication to a host system over a significant distance with "plug-and-play" adaptation and simplicity. The system is net-workable. It may be inter-connectable with other gas sample conditioning devices (particle filters, valves, flow and pressure sensors), local maintenance control points, and can provide gas leak monitoring via the internet. The detector is robust. It can maintain accuracy in a high electromagnetic interference (EMI) environment such as in the vicinity of electrical power distribution sub-stations where very strong electrical and magnetic fields are present. The detector has high sensitivity. It offers sub-ppm (parts-per-million) level detection which is 100 to 10,000 times better than related art technology, such as conventional gas chromatographs which may offer a sensitivity between the 1 to 10 ppm range. The detector is, among other things, a lower-power, faster, and more compact, more sensitive and affordable version of a gas chromatograph. It may also be lower power-consuming and faster than previous versions of the present kind of phased-heater detectors which require heavy batteries needing many changes or recharges, which may be avoided in the present detector. The latter detector may have structural integrity, and have very low or no risk of leakage in the application of detecting and analyzing pressurized fluid samples, over a very large differential pressure range.

In the leak detector, a small pump, such as a Honeywell MesoPump™ preferably draws a sample into the sensor system, while only a portion of it flows through the phased heater sensor at a rate controlled by the valve (which could be a Honeywell MesoValve™ or Hoerbiger PiezoValve™). This enables fast sample acquisition despite long sampling lines, yet provides a regulated, approximately 1 to 3 cm³/min flow for the leak detector. The pump of the leak detector may be arranged to draw sample gas through a filter in such a way as to provide both fast sample acquisition for and regulated flow through the phased heater sensor.

As the sample pump draws sample gas through the leak detector, the gas is expanded and thus increases its volume and linear velocity. The control circuit is designed to compensate for this change in velocity to keep the heater "wave" in sync with the varying gas velocity in the detector. To compensate for the change in sample gas volume as it is forced through the heater channels, its electronics may need to adjust either the flow control and/or the heater "wave" speed to keep the internal gas flow velocity in sync with the heater "wave".

During leak survey operation, present detector's ability (like any other slower GCs) may sense multiple trace constituents of air such as about 330 to 700 ppm of $CO_2$, about 1 to 2 ppm of $CH_4$ and about 0.5 to 2.5 percent of $H_2O$.

This enables on-line calibration of the output elution times as well as checking of the presence of additional peaks such as ethane, indicating natural gas, propane or other gas pipeline leak. The ratio of sample gas constituent peak heights thus reveals clues about the source of the trace gases, which could include car exhaust or gasoline vapors.

The leak detector may have sensitivity, speed, portability and low power that make it especially well suited for safety-mandated periodic leak surveys of natural gas or propane gas leaks along transmission or distribution pipeline systems, and gas leaks in chemical process plants.

The detector may in its leak sensing application use some or all sample gas constituents (and their peak ratios) as calibration markers (elution time identifies the nature of the gas constituents) and/or as leak source identifiers. If the presence alone of a certain peak such as methane (which is present in mountain air at about one to two ppm) may not be enough information to indicate that the source of that constituent is from swamp gas, natural/pipeline gas or another fluid.

The proposed leak sensor may be used as a portable device or installed at a fixed location. In contrast to comparable related art sensors, it is more compact than portable flame ionization detectors without requiring the bulkiness of hydrogen tanks, faster and more sensitive than hot-filament or metal oxide combustible gas sensors, and much faster, more compact and more power-thrifty than conventional and/or portable GCs.

BRIEF DESCRIPTION OF THE DRAWING

FIG. 13 shows a table revealing various power consumption levels of parts of the gas leak detector.

DESCRIPTION

Figure 1:
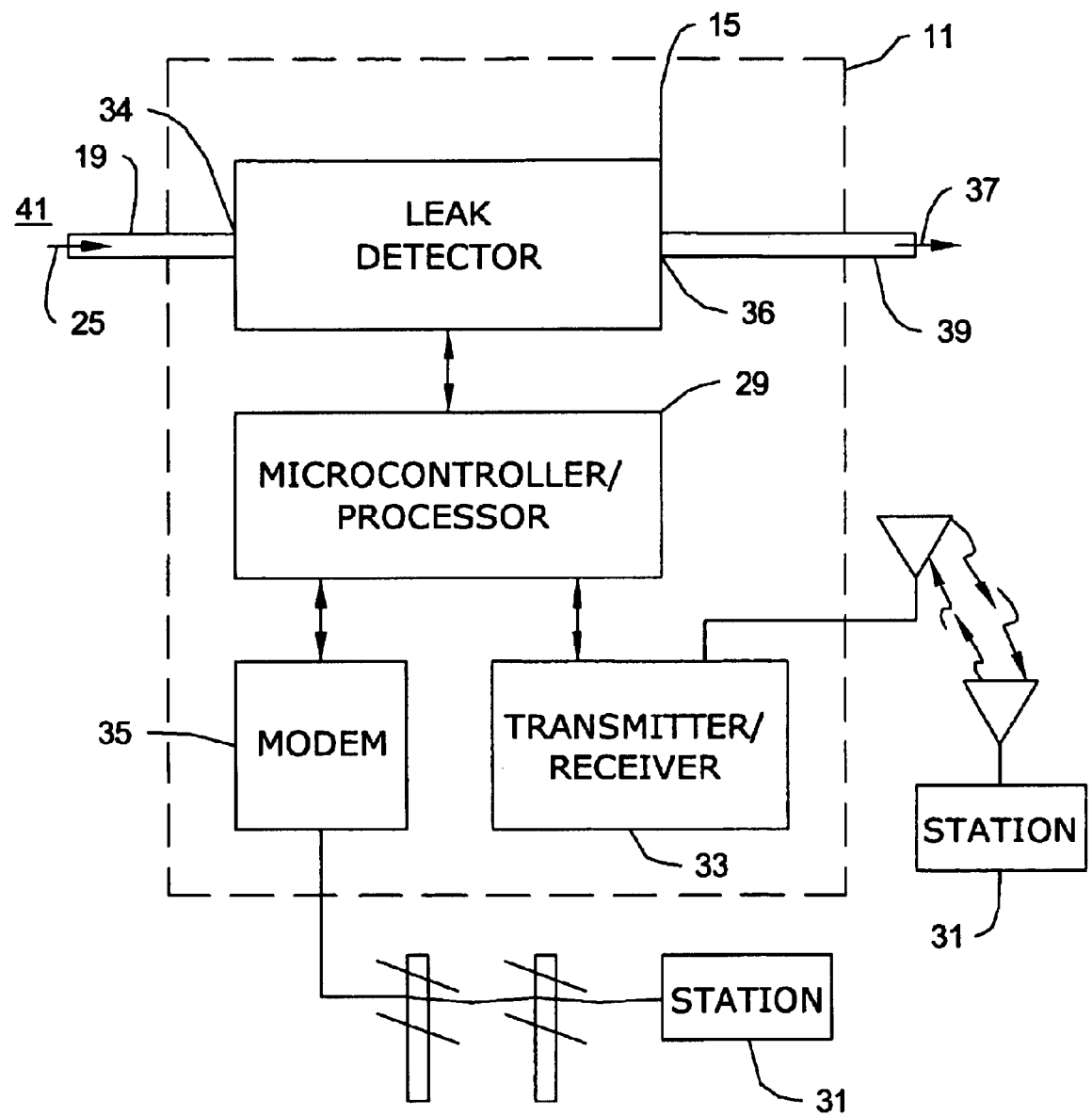
FIG. 1 is a block diagram of a possible leak detector monitor system.

FIG. 1 reveals an illustrative diagram of a low power leak detector system 11. An input fluid 25 from an ambient space or volume 41 may enter a conduit or tube 19 which is connected to an input 34 of a low power leak detector 15. Fluid 25 is processed by detector 15. Processed fluid 37 exits output 36 of detector 15 and is exhausted to a volume, wherever designated, via a conduit or tube 39. "Fluid" may be used as a generic term that includes gases and liquids as species. The results or findings may be sent to a microcontroller or processor 29 for analysis. Microcontroller or processor 29 may send various signals to detector 36 for control, adjustment, calibration or other purposes. The analysis calculations, results or other information may be sent to modem 35 for conversion into signals to be sent to a station 31 via lines, fiber or other like media. Also, such output to modem 35 may be instead or simultaneously sent to transmitter 33 for wireless transmission to a station 31, together with information on the actual location of the detector obtained, e.g., via GPS, especially if it is being used as a portable device. Also, stations 31 may send various signals to modem 35 and receiver 33, which may be passed on to microcontroller or processor 29 for control, adjustment, calibration or other purposes.

Figure 2:
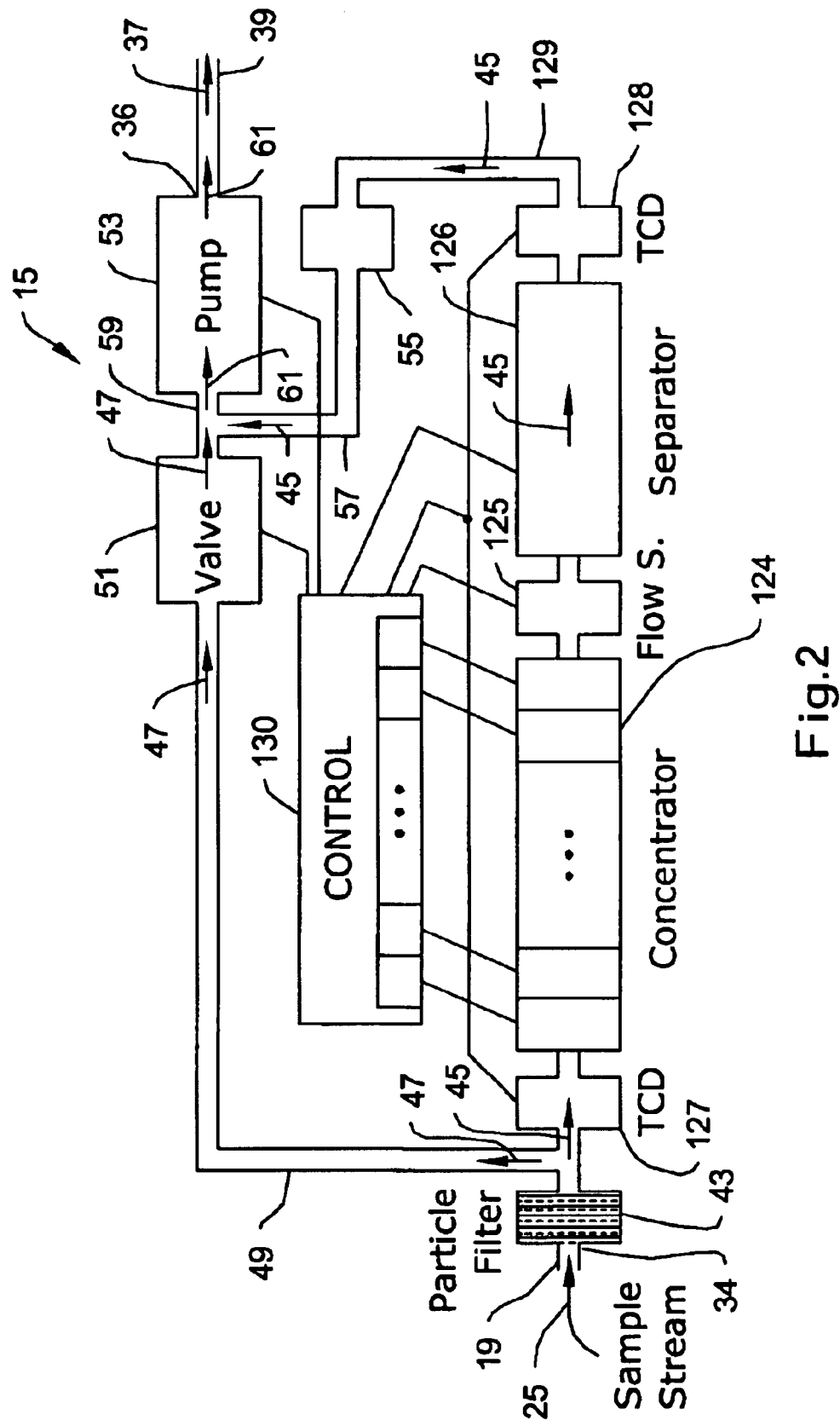
FIG. 2 shows details of a micro gas detector apparatus.

FIG. 2 reveals micro gas leak detection apparatus 15. Sample stream 25 containing gas from a possible leak may enter input port 34 from pipe or pick-up tube 19. There may be a particle filter 43 for removing dirt and other particles from the stream of fluid 25 that is to enter apparatus 15. This removal is for the protection of the apparatus and the filtering should not reduce the apparatus' ability to accurately analyze the composition of fluid 25. Dirty fluid (with suspended solid or liquid non-volatile particles) could possibly impair proper sensor function. A portion 45 of fluid 25 flows through a thermal-conductivity detector or sensor 127 and a portion 47 of fluid 25 flows through tube 49 to a one-way valve 51. By placing a "T" tube immediately adjacent to the inlet of fluid 45, sampling with minimal time delay is achieved, because of the relatively higher flow of fluid 47, which helps to shorten the filter purge time. Pump 53 causes fluid 47 to flow from the output of particle filter 43 through tube 49 and valve 51. Modulating valve 51 controls the flow through the sensor via tube 57 by adjusting the suction pressure of pump 55 in tube 129. The above flow configuration may thus achieve two benefits simultaneously. These benefits may include minimal sampling delay time and flow control. Pump 55 causes fluid 45 to flow from the output of filter 43 through detector 127, concentrator 124, flow sensor 125, separator 126, thermal-conductivity detector or sensor 128 and tube 129. Pump 55 pumps the fluid through tube 57 to tube 59 where it joins fluid 47 as a combined fluid 61. Pump 55 may be used in the system, depending on suction capacity of pump 53 (10–300 cm3/min) and sufficiently low-flow-capacity of pump 55 (0.1–3 cm3/min). Fluid 61 is pumped to output port 36 by pump 53. Fluid 61 may flow out as stream 37 through exit tube or pipe 39. Data from detectors 127 and 128 may be sent to control 130, which in turn relays data to microcontroller and/or processor 29 for processing. Resultant information may be sent to station 31.

Figure 3:
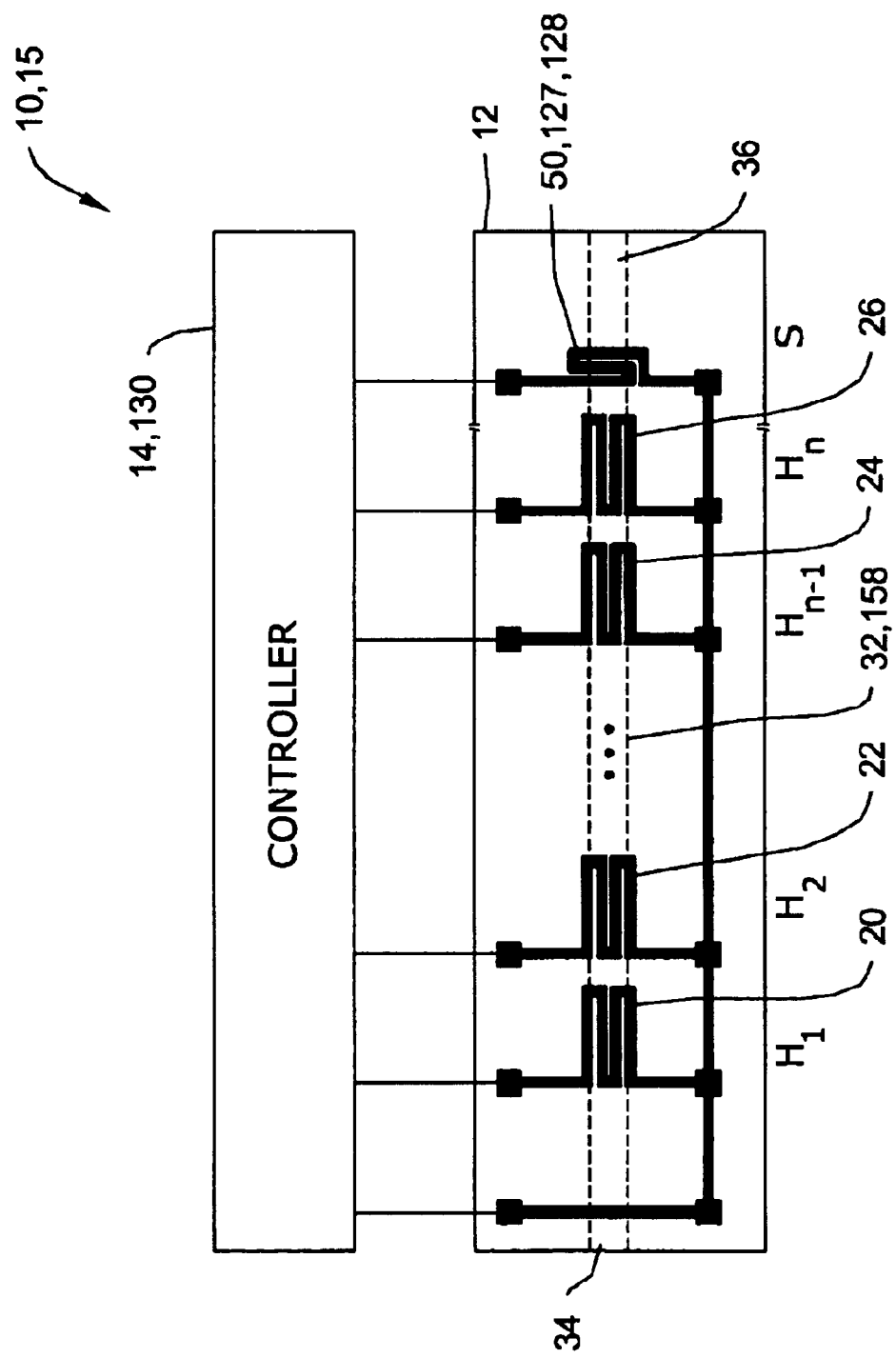
FIG. 3 is a layout to show the principle of operation of an illustrative sensor apparatus.
Figure 4:
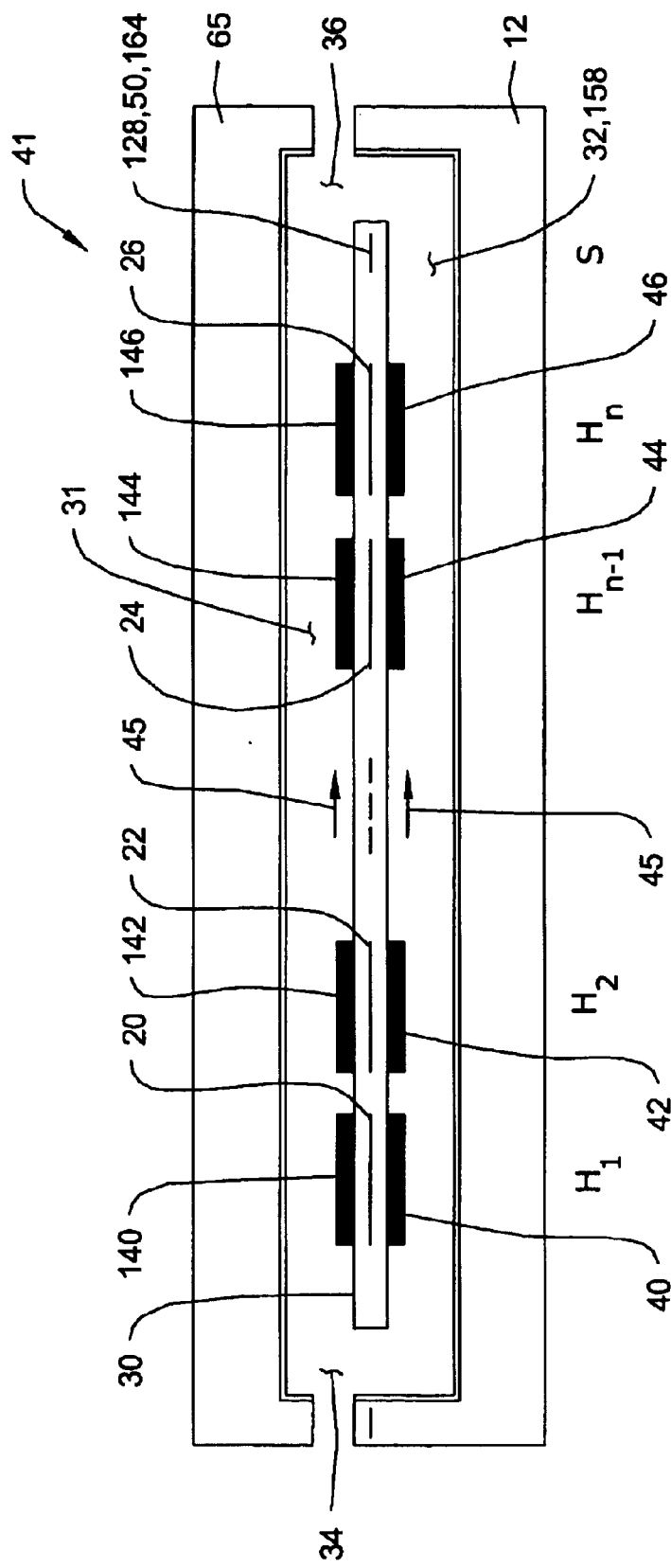
FIG. 4 is a cross-sectional side view of the illustrative sensor apparatus in FIG. 3.
Figure 5:
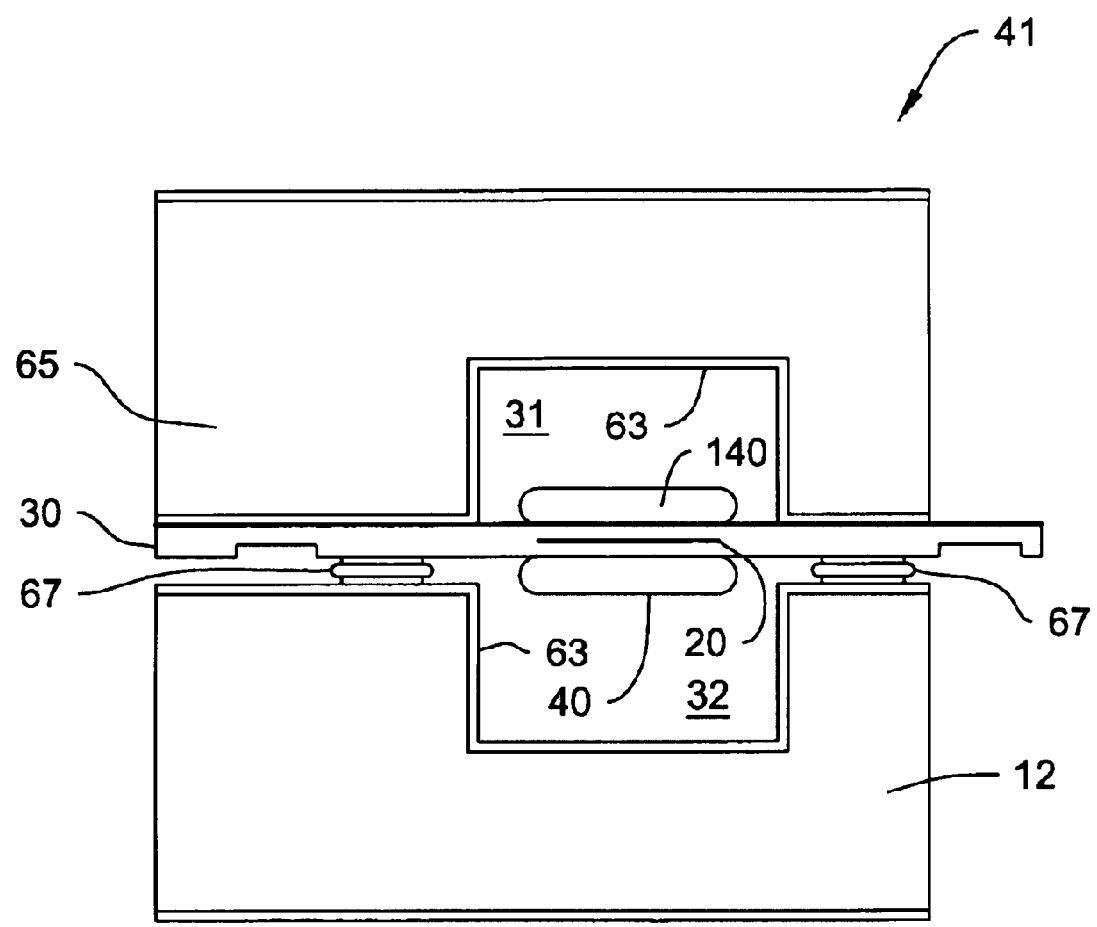
FIG. 5 is a cross-sectional end view of the illustrative sensor apparatus of FIG. 3

FIG. 3 is a schematic diagram of part of the sensor apparatus 10 or 15, representing concentrator 124 or separator 126 in FIG. 2. The sensor apparatus may include a substrate 12 and a controller 14. Controller 14 may or may not be incorporated into substrate 12. Substrate 12 may have a number of thin film heater elements 20, 22, 24, and 26 positioned thereon. While only four heater elements are shown, any number of heater elements may be provided, for instance, between two and one thousand, but typically in the 20–100 range. Heater elements 20, 22, 24, and 26 may be fabricated of any suitable electrical conductor, stable metal, or alloy film, such as a nickel-iron alloy sometimes referred to as permalloy having a composition of eighty percent nickel and twenty percent iron, platinum, platinum silicide, and polysilicon. Heater elements 20, 22, 24, and 26 may be provided on a thin, low-thermal mass, low-in-plane thermal conduction, support member 30, as shown in FIGS. 4 and 5. Support member or membrane may be made from $Si_3N_4$ or other appropriate or like material. The heater elements may be made from Pt or other appropriate or like material.

FIGS. 4 and 5 reveal a double-channel phased heater mechanism 41 having channels 31 and 32. Substrate 12 and portion or wafer 65 have defined channels 31 and 32 for receiving a streaming sample fluid 45. The channels may be fabricated by selectively etching silicon channel wafer or substrate 12 beneath support member 30 and channel wafer or portion 65 above the support member. The channels include an entry port 34 and an exhaust port 36 for streaming sample fluid 45.

The sensor apparatus may also include a number of interactive elements inside channels 31 and 32 so that they are exposed to the streaming sample fluid 45. Each of the interactive elements may be positioned adjacent, i.e., for closest possible contact, to a corresponding heater element. For example, as in FIG. 4, interactive elements 40, 42, 44, and 46 may be provided on the lower surface of support member 30 in channel 32, and adjacent to heater elements 20, 22, 24, and 26, respectively. Additionally, interactive elements 140, 142, 144, and 146 may be provided on the upper surface of support member 30 in channel 31, and adjacent to heater elements 20, 22, 24, and 26, respectively. There may be other channels with additional interactive film elements which are not shown in the present illustrative example. The interactive elements may be formed from any number of films commonly used in liquid or gas chromatography, such as silica gel, polymethylsiloxane, polydimethylsiloxane, polyethyleneglycol, porous silica, Nanoglass™, active carbon, other similar polymeric substances. Furthermore, the above interactive substances may be modified by suitable dopants to achieve varying degrees of polarity and/or hydrophobicity, to achieve optimal adsorption and/or separation of targeted analytes.

FIG. 5 shows a cross-section end view of phased heater mechanism 41. Support member 30 is attached to top structure 65. Anchors 67 hold support member 30 in place relative to channel 31. Fewer anchor 67 points minimize heat conduction losses from support 30 to other portions of structure 41. In contrast to a normal anchoring scheme, the present example has a reduction of anchor points that may result in the saving about 1.5 times of the remaining heater element input power.

Interactive film elements may be formed by passing a stream of material carrying the desired sorbent material through channel 32. This provides an interactive layer throughout the channel. If separate interactive elements are desired, the coating may be selectively "developed" by providing a temperature change to the coating, via heater elements 20, 22, 24 and 26. After the coating is developed, a stream of solvents may be provided through channel 32 to remove the coating everywhere except where the coating has been developed or polymerized with suitable solvents such as acetone, leaving only the sorbent material that is adjacent the heater elements. A coating 63 of a non-adsorbing, thermal insulating material may be applied to the inside walls of channels 31 and 32, except where there is adsorber coated surfaces, by design, such as the interactive elements. This coating may reduce the needed heater element power by about 1.5 times. The material should have thermal conduction that is substantially less than the material used in the channel walls. The latter may be silicon. Alternative materials for coating 63 may include $SiC_2$ or other thermal oxides. Coating 63 may reduce power used for the heater elements in support 30. A minimizing or reduction of the size (width, length and thickness) of the heater element membranes as well as the adsorber film, while retaining a reasonable ratio of mobile/stationary phase volume, may result in about a four times power reduction. The minimized or reduced adsorber film thickness may reduce the time needed for adsorption-desorption and save about 1.5 times in energy needed per fluid analysis. The use of a particularly thrifty but adequately function pump 53 and/or 55 and 120, which may run only about or less than one second before he start of a concentrator and/or measurement cycle of detector system 11, and the use of low-power electronics for control 130 and/or microcontroller/processor (which uses a sleep mode when not in use) may result in about a two times reduction in such power.

The table in FIG. 13 shows the overall power needed to run leak detector system 11 to similar system to be about 100 milliwatts or less with the mentioned herein design features of the system running one analysis cycle every three seconds. As shown in the table, energy conservation measures on the system 11 can reduce the energy needed per analysis (initiated once every 3 seconds) from about 1.7 Joules and peak power of about 1280 mW, down to about 0.4 Joules, with peak power of 220 mW.

Controller 14 or 130 may be electrically connected to each of the heater elements 20, 22, 24, 26, and detector 50 as shown in FIG. 3. Controller 14 or 130 may energize heater elements 20, 22, 24, and 26 in a time phased sequence (see bottom of FIG. 6) such that each of the corresponding interactive elements 40, 42, 44, and 46 become heated and desorb selected constituents into a streaming sample fluid 45 at about the time when an upstream concentration pulse, produced by one or more upstream interactive elements, reaches the interactive element. Any number of interactive elements may be used to achieve the desired concentration of constituent gases in the concentration pulse. The resulting concentration pulse may be provided to detector 50, 128, 164 for detection and analysis. Detector 50, 127, 128 or 164 may be a thermal conductivity detector, discharge ionization detector, or any other type of detector such as that typically used in gas or fluid chromatography.

Figure 6:
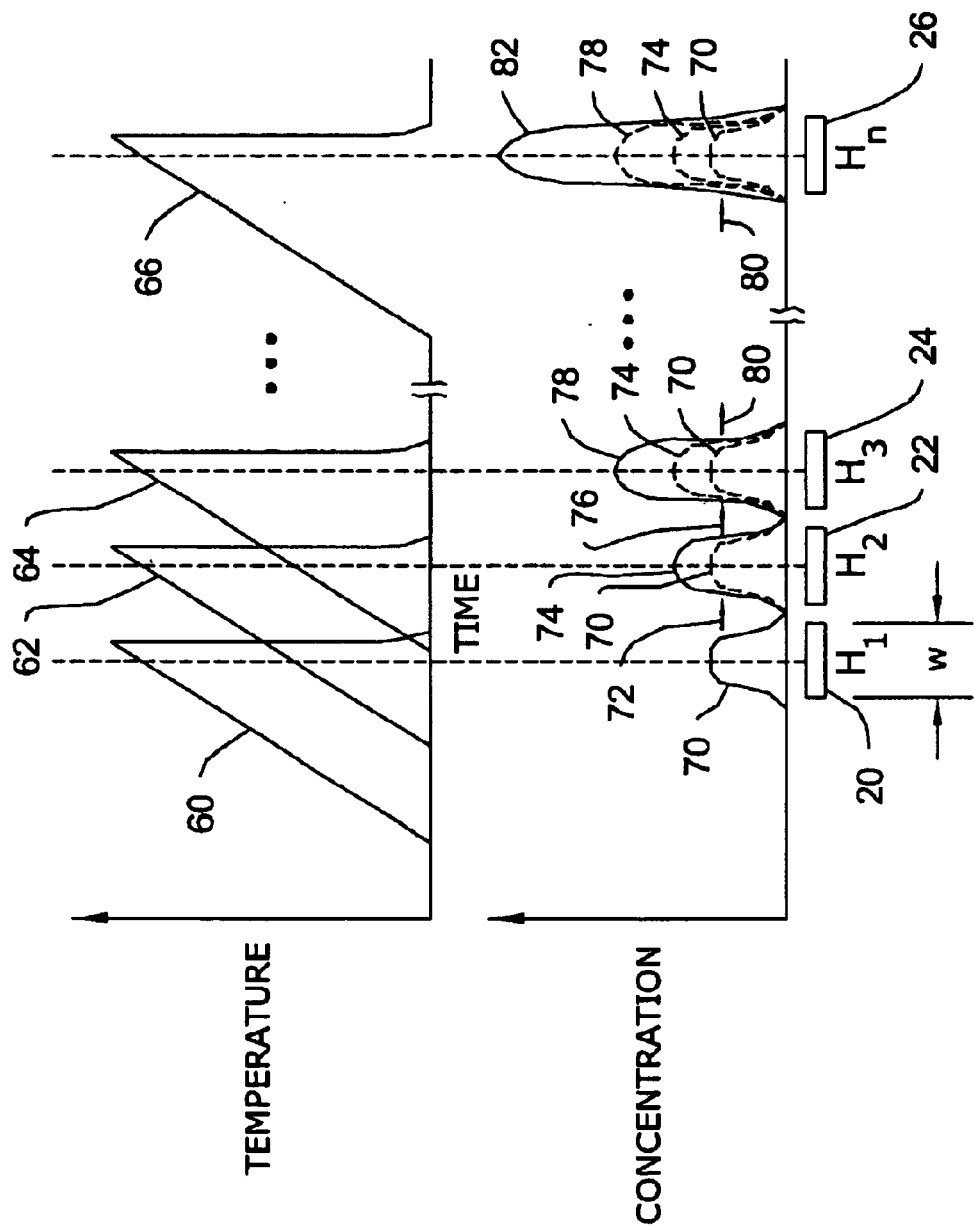
FIG. 6 is a graph showing illustrative heater temperatures, along with corresponding concentration pulses produced at each heater element of the sensor apparatus.

FIG. 6 is a graph showing illustrative heater temperatures, along with corresponding concentration pulses produced at each heater element. As indicated above, controller 14 or 130 may energize heater elements 20, 22, 24, and 26 in a time phased sequence. Illustrative time phased heater temperatures for heater elements 20, 22, 24, and 26 are shown by temperature profiles or lines 60, 62, 64, and 66, respectively.

In the example shown, controller 14, 130 (FIG. 3) may first energize first heater element 20 to increase its temperature as shown at line 60 of FIG. 6. Since first heater element 20 is thermally coupled to first interactive element 40, the first interactive element desorbs selected constituents into the streaming sample fluid 45 to produce a first concentration pulse 70 at the detector 128 or 50 or 164, if no other heater elements were to be pulsed. The streaming sample fluid carries the first concentration pulse 70 downstream toward second heater element 22, as shown by arrow 72.

Controller 14 (or 130) may next energize second heater element 22 to increase its temperature as shown at line 62, starting at or before the energy pulse on element 20 has been stopped. Since second heater element 22 is thermally coupled to second interactive element 42, the second interactive element also desorbs selected constituents into streaming sample fluid 45 to produce a second concentration pulse. Controller 14, 130 may energize second heater element 22 such that the second concentration pulse substantially overlaps first concentration pulse 70 to produce a higher concentration pulse 74, as shown in FIG. 6. The streaming sample fluid carries larger concentration pulse 74 downstream toward third heater element 24, as shown by arrow 76.

Controller 14, 130 may then energize third heater element 24 to increase its temperature as shown at line 64 in FIG. 6. Since third heater element 24 is thermally coupled to third interactive element 44, third interactive element 44 may desorb selected constituents into the streaming sample fluid to produce a third concentration pulse. Controller 14, 130 may energize third heater element 24 such that the third concentration pulse substantially overlaps larger concentration pulse 74 provided by first and second heater elements 20 and 22 to produce an even larger concentration pulse 78. The streaming sample fluid carries this larger concentration pulse 78 downstream toward an "Nth" heater element 26, as shown by arrow 80.

Controller 14, 130 may then energize "Nth" heater element 26 to increase its temperature as shown at line 66. Since "Nth" heater element 26 is thermally coupled to an "N-th" interactive element 46, "N-th" interactive element 46 may desorb selected constituents into streaming sample fluid 45 to produce an "N-th" concentration pulse. Controller 14, 130 may energize "N-th" heater element 26 such that the "N-th" concentration pulse substantially overlaps larger concentration pulse 78 provided by the previous N−1 interactive elements. The streaming sample fluid carries "N-th" concentration pulse 82 to either a separator 126 or a detector 50, 128 or 164, as described below.

As indicated above, heater elements 20, 22, 24, and 26 may have a common length. As such, controller 14, 130 can achieve equal temperatures of the heater elements by providing an equal voltage, current, or power pulse to each heater element. The voltage, current, or power pulse may have any desired shape including a triangular shape, a square shape, a bell shape, or any other shape. An approximately square shaped voltage, current, or power pulse is used to achieve temperature profiles 60, 62, 64, and 66 shown in FIG. 6.

Figure 7:
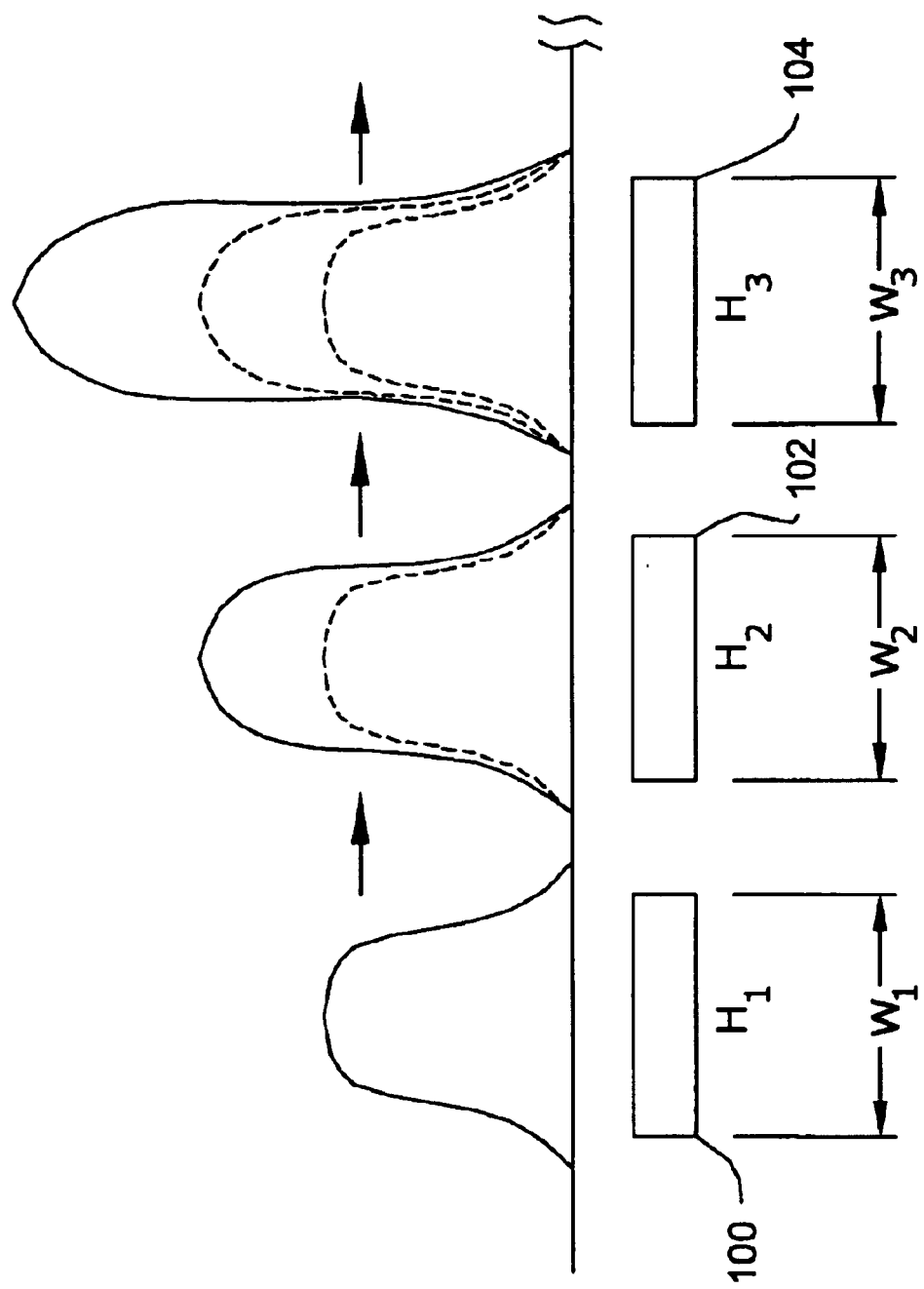
FIG. 7 is a graph showing a number of heater elements to illustrate their way of step-wise build-up on analyte concentration.

FIG. 7 is a graph showing a number of heater elements to illustrate, first, how the concentration increases stepwise as the desorption of subsequent elements is appropriately synchronized with the streaming sample fluid velocity and, second, how the lengths of individual elements are matched to the expected increased rate of mass diffusivity flux as the concentration levels and gradients increase. It should.be pointed out here that prior to the elements shown in FIG. 7, the analyte concentration may have been already magnified by a factor, F, by virtue of pulsing an initial element with a length F-times longer than the one shown as element 100 (H1 or, alternatively, by simultaneously pulsing elements 1, 2, . . . , F and collecting all the desorbed analyte with the still cool element 100 (H1), before pulsing it. It is recognized that each of the concentration pulses may tend to decrease in amplitude and increase in length when traveling down channel 32 due to diffusion. To accommodate this increased length, it is contemplated that the length of each successive heater element may be increased along the streaming sample fluid. For example, a second heater element 102 may have a length $W_2$ that is larger than a length $W_1$ of a first heater element 100. Likewise, a third heater element 104 may have a length $W_3$ that is larger than length $W_2$ of second heater element 102. Thus, it is contemplated that the length of each heater element 100, 102, and 104 may be increased, relative to the adjacent upstream heater element, by an amount that corresponds to the expected increased length of the concentration pulse of the upstream heater elements due to diffusion.

To simplify the control of the heater elements, the length of each successive heater element may be kept constant to produce the same overall heater resistance between heater elements, thereby allowing equal voltage, current, or power pulses to be used to produce similar temperature profiles. Alternatively, the heater elements may have different lengths, and the controller may provide different voltage, current, or power pulse amplitudes to the heater element to produce a similar temperature profile.

Figure 8:
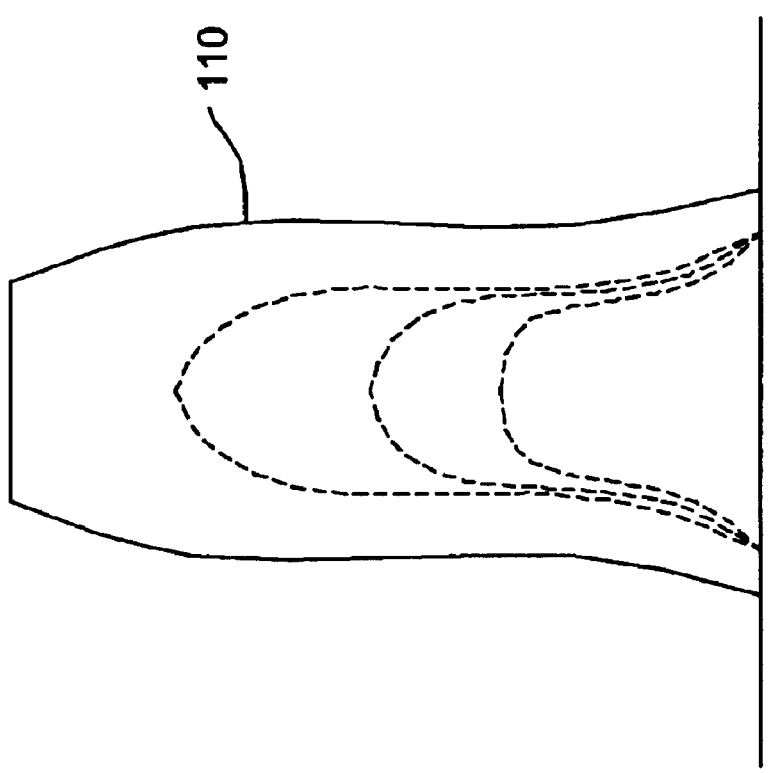
FIG. 8 is a graph showing a concentration pulse that reaches about a 100 percent concentration level.

FIG. 8 is a graph showing a concentration pulse 110 that achieves a 100 percent concentration level. It is recognized that even though concentration pulse 110 has achieved a predetermined concentration threshold, such as 100 percent, the concentration of the corresponding constituent can still be determined. To do so, detector 50, 128, 164 may detect the concentration pulse 110, and controller 14, 130 may integrate the output signal of the detector over time to determine the concentration of the corresponding constituent in the original sample of stream 45.

Heater elements 20, 22, 24 and 26 may be GC-film-coated on both the top and bottom sides so that the width and power dissipation of the heater element surface by about two times. The fabrication of these heater elements involves two coating steps, with the second step requiring wafer-to-wafer bonding and coating after protecting the first coat inside the second wafer and dissolving the first wafer.

Figure 9:
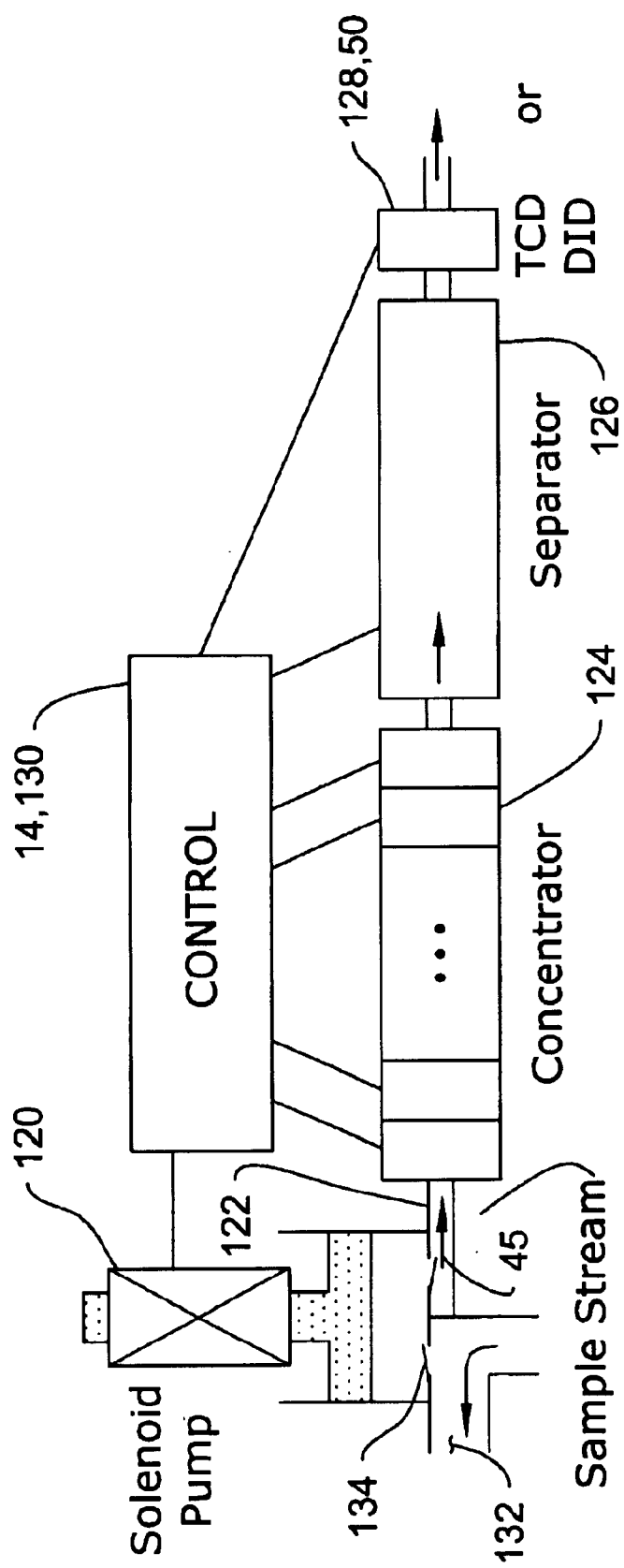
FIG. 9 is a layout of another illustrative sensor assembly.

FIG. 9 is a schematic view of another illustrative sensor assembly 15 similar to that of FIG. 3. The sensor assembly may include a simpler solenoid pump 120, a streaming sample fluid input 122, a concentrator 124, a separator 126, a detector 128, and a controller 14 or 130. At the request of the controller 14, 130, solenoid pump 120 may draw a sample 45 from a flue gas stream 132 through a one-way valve 134. Controller 14, 130 may then direct solenoid pump 120 to provide streaming sample fluid 45, at a desired pressure, to concentrator 124.

Concentrator 124 may include two or more interactive elements that are in communication with streaming sample fluid 45. Concentrator 124 also may include two or more heater elements that are in thermal communication with the interactive elements. When energized, each heater element heats a corresponding interactive element, causing the interactive element to desorb selected constituents into the streaming sample fluid. As described above, controller 14, 130 may energize the heater elements in a time phased sequence to provide an increased concentration pulse.

Streaming sample fluid 45 may carry the concentration pulse to separator 126. Separator 126 may separate selected constituents of the concentration pulse and provide the separated constituents to detector 50, 128, 164. This detector may provide a signal to controller 14, 130 indicating the concentration level of each constituent. Controller 14, 130 may determine the actual concentration level of each constituent in the original gas sample by dividing the sensed concentration level by the concentration amplification provided by the sorbent material of each interactive element and the multiplier effect provided by the phased heater arrangement.

Figure 10:
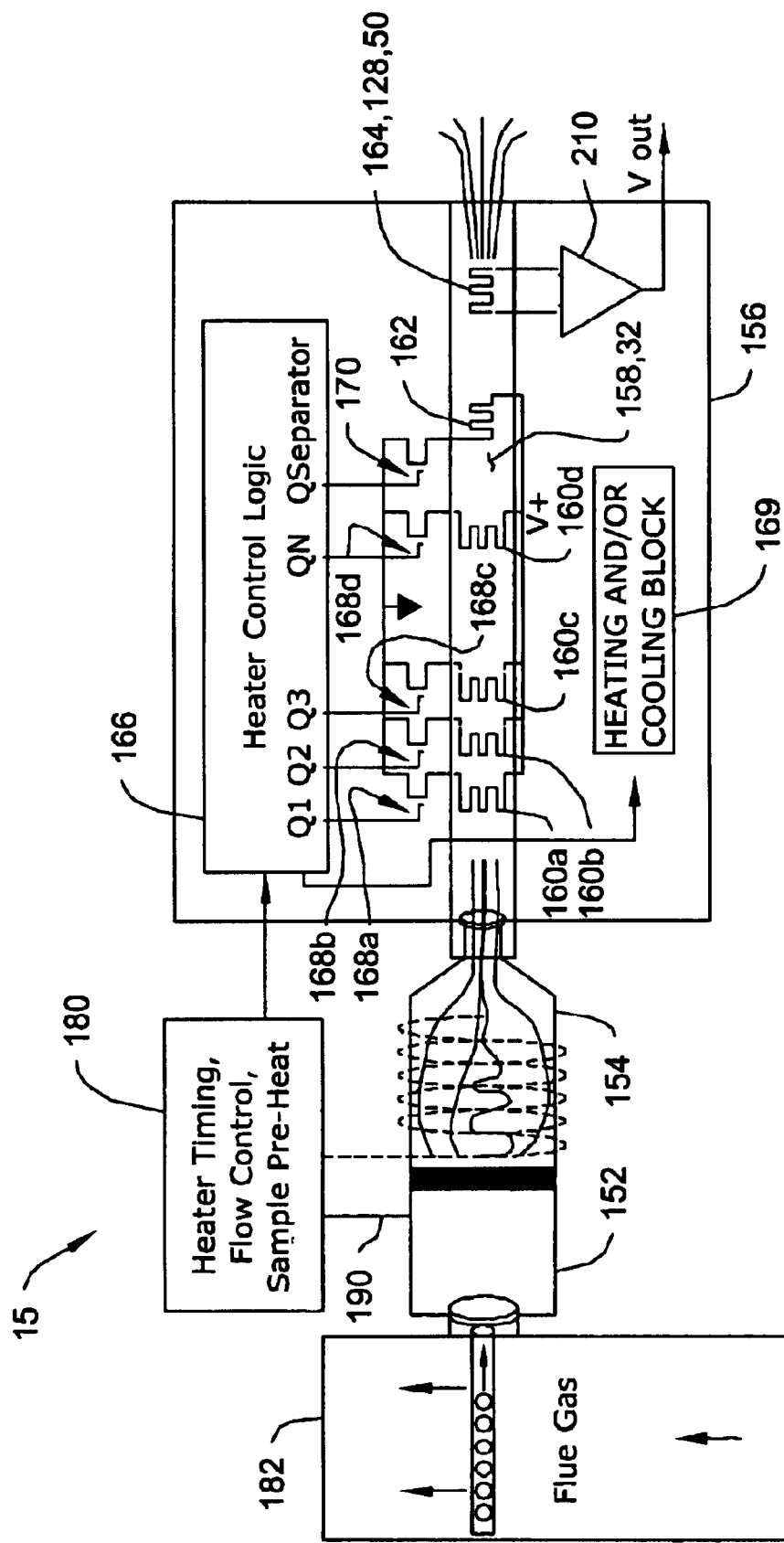
FIG. 10 is a schematic view of how to apply the sensor to sample a fluid stream (e.g., stack gas) for its gas composition analysis.
Figure 11:
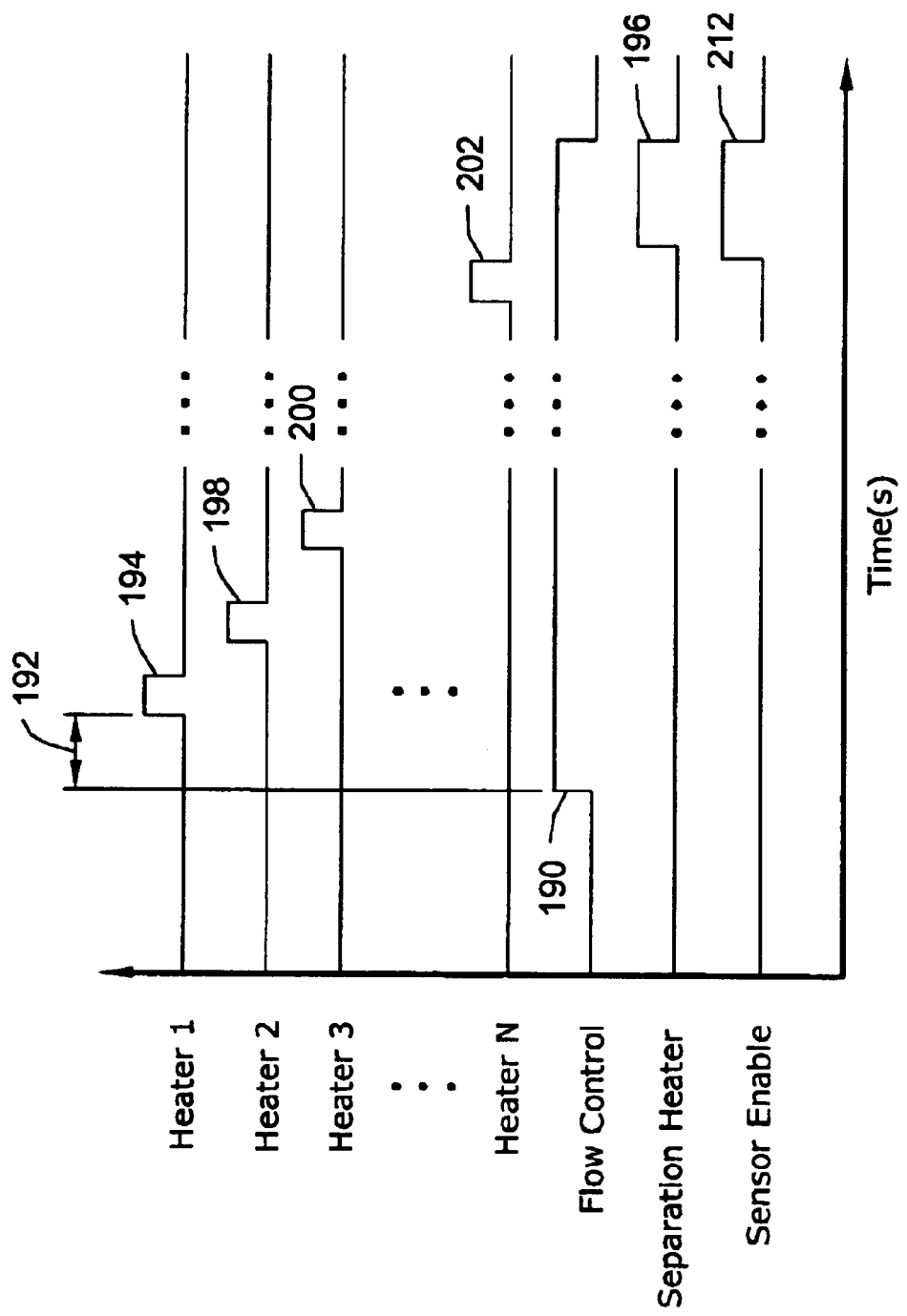
FIG. 11 is a timing chart showing the operation of the sensor assembly of FIG. 10.

FIG. 10 is a schematic view of another illustrative sensor assembly 15. FIG. 11 is a timing chart showing the operation of sensor assembly 15 of FIG. 10. Sensor assembly 15 may include a pump 152, a gas preheater 154, and a microbridge type integrated circuit chip 156. The microbridge type integrated circuit includes a channel 158, 32, a number of heater elements 160a, 160b, 160c, and 160d, a separation heater 162, and a detector 164, 128, 50. Each of heater elements 160a, 160b, 160c, and 160d, separation heater 162, and detector 164 are provided on a support member 30 that extends over the channel 158, 32 (e.g., FIG. 5). Interactive elements (not explicitly shown) are placed in channel 158, 32 and in thermal communication with each of heater elements 160a, 160b, 160c, and 160d.

Microbridge type integrated circuit chip 156 also may include a heater control block 166 and a number of energizing transistors 168a, 168b, 168c, 168d, and 170. Heater control block 166 can individually energize each of heater elements 160a, 160b, 160c, and 160d, by activating a corresponding energizing transistor 168a, 168b, 168c, 168d, respectively. Likewise, heater control block 166 can energize separation heater 162 by turning on transistor 170. Heating or cooling block 169 (of FIG. 10) complements preheater 154 in maintaining an average or overall temperature that is optimal for operation of sensor assembly 15.

A sensor assembly control block 180 directs the overall operation of sensor assembly 15. Sensor assembly control block 180 first asserts a flow control signal 190 to pump 152. Flow control signal 190 is shown in FIG. 11. In response, pump 152 draws a sample from flue 182 and provides the sample, at a desired pressure, to preheater 154 and eventually to channel 158, 32. Preheater 154 preheats and the heater maintains the sample gas at optimal operating element temperature and thus helps to prevent loss of sample due to condensation and to increase the amount of constituents that can be accumulated in each of the interactive elements.

The streaming sample fluid passes down channel 158, 32 for a predetermined time period 192 until the interactive elements reach a state of substantially saturation of adsorption of one or more constituents from the streaming sample fluid and reach equilibrium. Thereafter, sensor assembly control block 180 notifies heater control block 166 to begin heating the heater elements in a time phased sequence. Heater control block 166 first provides a first heater enable signal 194 and a separation heater enable signal 196, as shown in FIG. 11. First heater enable signal 194 turns on transistor 168a, and separation heater enable signal 196 turns on transistor 170. Transistor 168a provides current to first heater element 160a, causing first heater element 160a to increase in temperature. This heats the corresponding interactive element, which desorbs one or more constituents into the streaming sample fluid in the form of a first concentration pulse. The first concentration pulse is carried downstream toward second heater element 160b by the streaming sample fluid. This process is repeated for the 3rd, 4th and N-th elements.

Heater control block 166 then provides a second heater enable signal 198, which turns on transistor 168b. Transistor 168b provides current to second heater element 160b, causing second heater element 160b to increase in temperature. This heats the corresponding interactive element, which desorbs one or more constituents into the streaming sample fluid in the form of a second concentration pulse. Heater control block 166 may time second heater enable signal 198 such that the second concentration pulse substantially overlaps the first concentration pulse. Both the first and second concentration pulses are carried downstream toward third heater element 160c.

The timing of second heater enable signal 198 relative to first heater enable signal 194 may be established by prior calibration. However, the heater control block 166 may sense the resistance of second heater element 160b. It is recognized that the resistance of second heater element 160b will begin to change when the first concentration pulse arrives at second heater element 160b because the first concentration pulse is typically hotter than the streaming sample fluid. Once a predetermined resistance change is sensed in second heater element 160b, heater control block 166 may energize second heater element 160b via transistor 168b. The remaining heater enable signals may be likewise controlled.

Heater control block 166 may then provide a third heater enable signal 200, which turns on transistor 168c. Transistor 168c provides current to third heater element 160c, causing third heater element 160c to increase in temperature. This heats the corresponding interactive element, which desorbs one or more constituents into the streaming sample fluid in the front of a third concentration pulse. Heater control block 166 may time third heater enable signal 200 such that the third concentration pulse substantially overlaps the first and second concentration pulses. The first, second, and third substantially overlapping concentration pulses are carried downstream toward "Nth" heater element 160d.

Heater control block 166 may then provide an "Nth" heater enable signal 202, which turns on transistors 168c. Transistor 168c provides current to "Nth" heater element 160d, causing "Nth" heater element 160d to increase in temperature. This heats the corresponding interactive element, which desorbs one or more constituents into the streaming sample fluid in the form of an "Nth" concentration pulse. The heater control block 166 may time "Nth" heater enable signal 202 such that the "Nth" concentration pulse substantially overlaps the previously generated concentration pulses. The resulting concentration pulse is carried downstream to separator heater 162. Separator heater 162, in conjunction with the channel 158, may separate selected constituents in the concentration pulse into individual constituent components. The separator's temperature ramp should not start before the end of the Nth pulse to the Nth concentrator element. Thus, pulse 196 begins after pulse 202 ends, as shown in FIG. 11. The individual constituent components may include one or more compounds, depending on a number of factors including the sample gas provided.

Transistor 170 then energizes separation heater 162 at the beginning of pulse 196 in FIG. 11 resulting in the heater 162 temperature having an increasing amplitude from room temperature up to about 200 degrees C. (or other temperature of design) versus time up to about one-half of the length of pulse 196 and then to remain at that temperature for the remaining time of pulse 196. Heater 162 separates the various constituents into individual components, as described above. The separated constituents are carried downstream to detector 164 by the streaming sample fluid. Detector 164 may be a thermal conductivity detector, discharge ionization detector, or any other type of detector such as those commonly used in gas chromatography. Detector 164 may sense the concentration levels of each individual constituent component, and provides a corresponding signal to amplifier 210. Amplifier 210 may amplify the detector output signal and provide the detector output signal to a data processing unit for analysis. Heater control block 166 may provide a detector enable signal 212 to enable the detector only when the individual constituent components are present.

Figure 12:
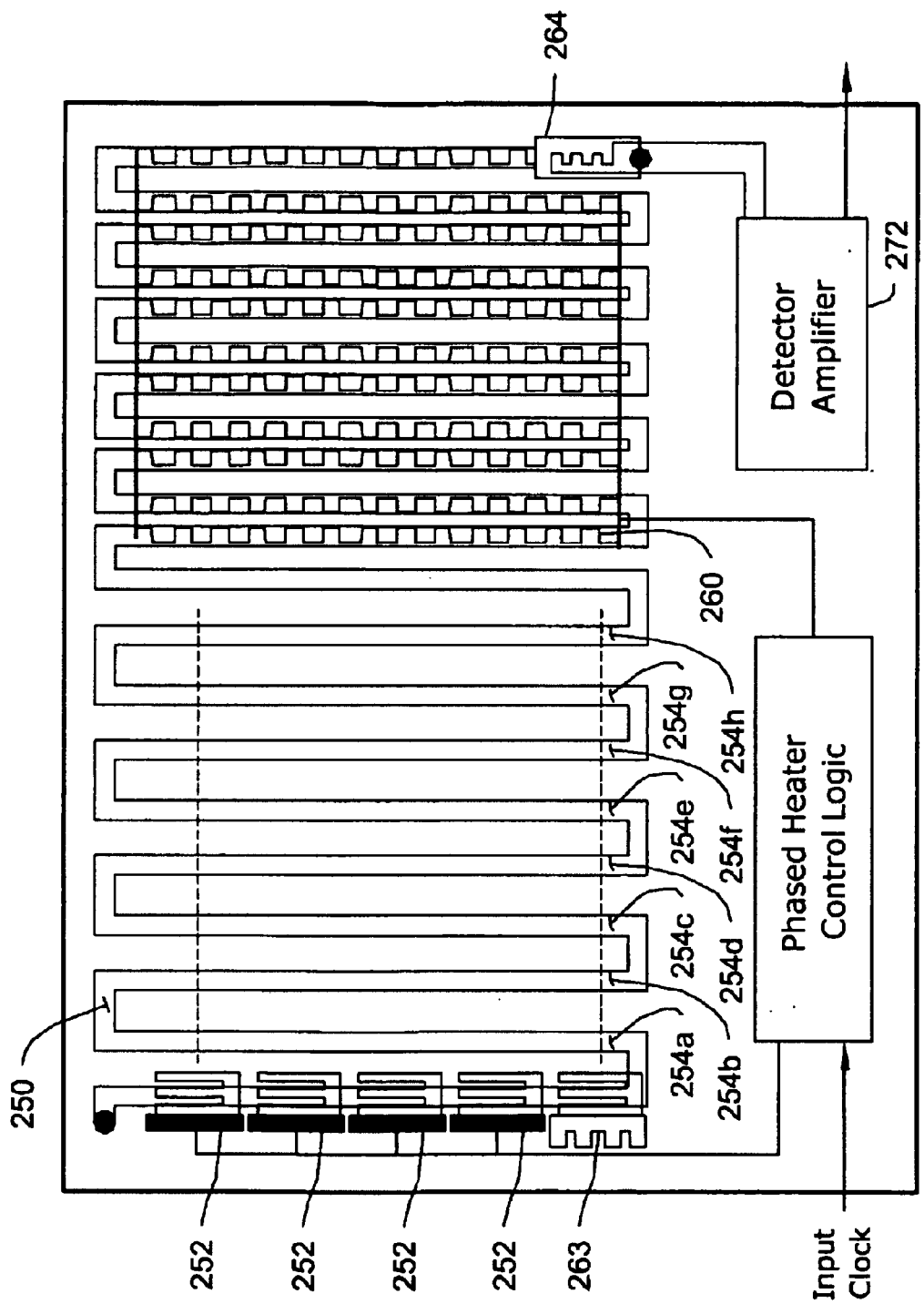
FIG. 12 is a basic layout of an integrated circuit that includes a sensor, a concentrator, a separator, and a sensor.

FIG. 12 is a basic layout of an integrated circuit that includes a concentrator, a separator, and a detector of micro gas apparatus 15. The integrated circuit may include a channel 250 that traverses back and forth across the chip as shown in FIG. 12. A first part of channel 250 has a detector 263 and number of heater elements 252 extending thereover on a support member, like support member 30 as described above. Interactive elements (not explicitly shown) are positioned in-channel 250 adjacent each of the heater elements. While only one column of heater elements 252 is shown, it is contemplated that each of the channel legs 254a–h may have a column of heater elements 252. There may be between two and one thousand heater elements spaced along channel 250.

A second downstream portion of channel 250 has a separation heater 260 extending thereover. The separation heater helps separate the various constituents in the concentration pulses provided by the heater elements 252. Finally, a detector 264 is provided over the channel 250 downstream of the separation heater 260. The detector may sense the concentration of each of the separated constituent components provided by the separator.

Because the concentrator, separator, and detector are provided on an integrated circuit, other conventional electronic circuits can be easily integrated therewith. A phased heater control block 270 and amplifier 272 may be fabricated on the same substrate. Chemical sensors, especially chemical microsensors as described, potentially afford many attractive features such as low cost, high sensitivity, ruggedness, and very small size.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A concentrator for concentrating one or more constituents of a fluid, comprising:
    two or more interactive elements spaced along in a first channel and exposed to the fluid in the first channel, each of the interactive elements having an interactive substance that adsorbs and desorbs selected constituents of the fluid depending on the temperature of the interactive element, wherein at least two of the interactive elements include the same interactive substance;
    two or more interactive elements spaced along in a second channel and exposed to the fluid in the second channel, each of the interactive elements having an interactive substance that adsorbs and desorbs selected constituents of the fluid depending on the temperature of the interactive element, wherein at least two of the interactive elements include the same interactive substance;
    a plurality heater elements, each heater element in thermal communication with a corresponding interactive element in the first channel and a corresponding interactive element in the second channel; and
    controller means coupled to the two or more heater elements for allowing the two or more interactive elements in the first channel and in the second channel to become exposed to the fluid in the first and second channels before energizing the heater elements in a time phased sequence.

2. A concentrator according to claim 1, wherein:
    the two or more interactive elements comprise different portions of the first channel exposed to and extending along at least part of the fluid; and
    the two or more interactive elements comprise different portions of the second channel exposed to and extending along at least part of the fluid.

3. A concentrator according to claim 2, wherein each of the plurality heater elements are in thermal communication with a corresponding portion of the first and second channels.

4. A concentrator according to claim 1, wherein the interactive elements are of equal length.

5. A concentrator according to claim 1, wherein the interactive elements are of unequal length.

6. A concentrator according to claim 1, wherein some of the interactive elements are of equal length and some of the interactive elements are of unequal length.

7. A concentrator for concentrating one or more constituents of a fluid, comprising:
    two or more interactive elements spaced along a first channel and exposed to the fluid in the first channel, each of the interactive elements having an interactive substance that adsorbs and desorbs selected constituents of the fluid depending on the temperature of the interactive element;
    two or more interactive elements spaced along a second channel and exposed to the fluid in the second channel, each of the interactive elements having an interactive substance that adsorbs and desorbs selected constituents of the fluid depending on the temperatu of the interactive element;
    a plurality of heater elements, each heater element in thermal communication with a corresponding interactive element in the first channel and a corresponding interactive element in the second channel; and
    controller means coupled to the plurality of heater elements for allowing the two or more interactive elements of the first channel and the two or more interactive elements of the second channel to become exposed to the fluid before energizing the heater elements in a time phased sequence, said controller means including first energizing means for energizing a first heater element, second energizing means for energizing a second heater element that is located downstream of the first heater element, and a controller for activating said first energizing means, which causes the corresponding first interactive element of the first channel to become heated and desorb selected constituents into the fluid which produces a first concentration pulse in the first channel that is carried by the fluid downstream toward the second heater element and causes the corresponding first interactive element of the second channel to become heated and desorb selected constituents into the fluid which produces a first concentration pulse in the second channel that is carried by the fluid downstream toward the second heater element, and for activating said second energizing means when the first concentration pulses reach the second heater elements.

8. A concentrator according to claim 7, wherein the first heater element and the second heater element include a resistive material.

9. A concentrator according to claim 8, wherein said first energizing means energizes said first heater clement by providing a first voltage, currents, or power pulse, and said second energizing means energizes said second heater element by providing a second voltage, current, or power pulse.

10. A concentrator for concentrating one or more constituents of a fluid, comprising:
    two or more interactive elements spaced along in a first channel and exposed to the fluid, each of the interactive elements include an interactive substance that adsorbs and desorbs selected constituents of the fluid depending on the temperature of the interactive element;

two or more interactive elements spaced along in a second channel and exposed to the fluid, each of the interactive elements include an interactive substance that adsorbs and desorbs selected constituents of the fluid depending on the temperature of the interactive element;

a plurality of heater elements, each heater element in thermal communication with a corresponding interactive element in the first channel and a corresponding interactive element in the second channel; and controller means coupled to the plurality of heater elements for energizing the heater elements in a time phased sequence, said controller means including first energizing means for energizing a first heater element with a first energy pulse, second energizing means for energizing a second heater element that is located downstream of the first heater element with a second energy pulse, and a controller for activating said first energizing means, which causes the corresponding interactive element of the first channel to become heated and desorb selected constituents into the fluid which produces a first concentration pulse in the first channel and causes the corresponding interactive element of the second channel to become heated and desorb selected constituents into the fluid which produces a first concentration pulse in the first channel which are carried by the fluid downstream toward the second heater element, and for activating said second energizing means when the first concentration pulses reach the second heater elements, wherein the first energy pulse and the second energy pulse result in triangular shaped temperature pulses of the heater elements.

11. A concentrator for concentrating one or more constituents of a fluid, comprising:

two or more interactive elements spaced along in a first channel and exposed to the fluid, each of the interactive elements including an interactive substance that adsorbs and desorbs selected constituents of the fluid depending on the temperature of the interactive element;

two or more interactive elements spaced along in a second channel and exposed to the fluid, each of the interactive elements including an interactive substance that adsorbs and desorbs selected constituents of the fluid depending on the temperature of the interactive element;

a plurality of heater elements, each heater element in thermal communication with a corresponding interactive element of the first channel and a corresponding interactive element of the second channel; and controller means coupled to the plurality of heater elements for energizing the heater elements in a time phased sequence, said controller means including first energizing means for energizing a first heater element with a first energy pulse, second energizing means for energizing a second heater element that is located downstream of the first heater element with a second energy pulse, and a controller for activating said first energizing means, which causes the corresponding interactive elements to become heated and desorb selected constituents into the fluid which produces first concentration pulses that are carried by the fluid downstream toward the second heater element, and for activating said second energizing means when the first concentration pulses reach the second heater elements, wherein the first energy pulse and the second energy pulse result in square shape temperature pulses of the heater elements.

12. A concentrator for concentrating one or more constituents of a fluid, comprising:

two or more interactive elements spaced along a first channel and exposed to the fluid, each of the interactive elements having an interactive substance that adsorbs and desorbs selected constituents of the fluid depending on the temperature of the interactive element;

two or more interactive elements spaced along a second channel and exposed to the fluid, each of the interactive elements having an interactive substance that adsorbs and desorbs selected constituents of the fluid depending on the temperature of the interactive element;

a plurality of heater elements, each heater element in thermal communication with a corresponding interactive element of the first channel and a corresponding interactive element of the second channel; and controller means coupled to the plurality of heater elements for energizing the heater elements in a time phased sequence, said controller means including first energizing means for energizing a first heater element with a first energy pulse, second energizing means for energizing a second heater element that is located downstream of the first heater element with a second energy pulse, and a controller for activating said first energizing means, which causes the corresponding interactive elements of the first and second channels, respectively, to become heated and desorb selected constituents into the fluid which produces a first concentration pulse in the first and second channels that is carried by the fluid downstream toward the second heater elements, and for activating said second energizing means when the first concentration pulse reaches the second heater element, wherein the first energy pulse and the second energy pulse result in bell shaped temperature pulses of the heater elements.

13. A concentrator for concentrating one or more constituents of a fluid, comprising:

two or more interactive elements spaced along in a plurality of channels and exposed to the fluid, wherein each of the interactive elements includes an interactive substance that adsorbs and desorbs selected constituents of the fluid depending on the temperature of the interactive element wherein each of the interactive elements has a length that is greater than the length of each interactive element located further upstream in the fluid;

two or more heater elements, each heater element in thermal communication with a corresponding interactive element; and a controller coupled to the plurality of heater elements for energizing the heater elements in a time phased sequence.

14. A sensor assembly for sensing the enhanced concentration of one or more constituents in a fluid, comprising:

two or more interactive elements spaced along in a first channel and exposed to the fluid, each of the interactive elements having an interactive substance that adsorbs and desorbs selected constituents of the fluid depending on the temperature of the interactive element;

two or more interactive elements spaced along in a second channel and exposed to the fluid, each of the interactive elements having an interactive substance that adsorbs and desorbs selected constituents of the fluid depending on the temperature of the interactive element;

a plurality of heater elements, each heater element in thermal communication with a corresponding interactive element of the first channel and a corresponding interactive element of the second channel;

controller means coupled to the plurality of heater elements for allowing the two or more interactive elements in each channel to become exposed to the fluid before energizing the heater elements in a time phased sequence such that each of the downstream interactive elements becomes heated and desorbs selected constituents into the fluid at substantially the time that an upstream concentration pulse, produced by one or more upstream interactive elements, reaches the downstream interactive element;

separator means for separating selected constituents of one of the concentration pulses provided by one or more of the interactive elements into individual constituent components; and detector means for sensing the concentration of one or more of the individual constituent components.

15. A sensor assembly according to claim 14, wherein said detector means includes a thermal conductivity detector.

16. A sensor assembly according to claim 14, further comprising a pump for providing the fluid.

17. A sensor assembly according to claim 16, wherein the pump is an efficient pump that runs only as needed during a concentrator measurement cycle.

18. A sensor assembly according to claim 14, wherein the fluid is driven by thermal convection.

19. A sensor assembly according to claim 14, further includes a preheater for preheating at least a portion of the fluid.

20. A sensor assembly according to claim 19, wherein said preheater heats the fluid throughout the sensor assembly.

21. A sensor assembly according to claim 19, wherein said preheater heats the fluid only in the separation means.

22. A sensor assembly according to claim 14, further includes a cooler for cooling at least a portion of the fluid.

23. A sensor assembly according to claim 14, wherein said controller means is in an inactive sleep mode when not energizing the heater elements.

24. A method for concentrating one or more constituents of a fluid, the method comprising:

providing sets of two or more interactive elements, the interactive elements of each set spaced along in a channel of a plurality of channels, respectively, and exposed to the fluid, each of the interactive elements having an interactive substance that adsorbs and desorbs selected constituents of the fluid depending on the temperature of the interactive element, where at least two of the interactive elements include the same interactive substance;

waiting for the interactive substance to adsorb one or more constituents from the fluid; and heating the two or more interactive elements of each set in a time phased sequence.

25. A method for concentrating one or more constituents of a fluid, the method comprising:

providing two or more interactive elements spaced along in each channel of a plurality of channels and exposed to the fluid, each of the interactive elements having an interactive substance that adsorbs and desorbs selected constituents of the fluid depending on the temperature of the interactive element, where at least two of the interactive elements incorporate the same interactive substance;

waiting for the interactive substance to adsorb one or more constituents from the fluid; and heating the two or more interactive elements of each channel in a time phased sequence, wherein said heating comprises:

heating an upstream interactive element, which causes the upstream interactive element to desorb selected constituents into the fluid to produce a first concentration pulse that is carried by the fluid downstream toward a downstream interactive element; and heating the downstream interactive element when the first concentration pulse reaches the downstream interactive element, which causes the downstream interactive element to desorb selected constituents into the fluid and at least partially overlap the first concentration pulse to produce a second concentration pulse that is carried by the fluid downstream.

26. A method for concentrating one or more constituents of a fluid, the method comprising:

providing N interactive elements for each of M channels, wherein N and M are greater than one, each of the N interactive elements being spaced along in each channel, respectively, and exposed to the fluid, each of the N interactive elements including an interactive substance that adsorbs and desorbs selected constituents of the fluid depending on the temperature of the interactive element such that, when heated, each of the N interactive elements desorb selected constituents into the fluid to produce a corresponding concentration pulse that is carried by the fluid downstream toward a downstream interactive element;

exposing the N interactive elements of each channel to the fluid;

waiting for the N interactive elements of each channel to adsorb one or more constituents from the fluid; and heating the N interactive elements of each channel in a time phased sequence whereby each of the downstream interactive elements is heated when the concentration pulse of the respective channel provided by one or more of the upstream interactive elements reaches the downstream interactive element.

27. A method according to claim 26, further comprising separating selected constituents of the concentration pulse provided by the one or more of the N interactive elements of each channel into individual components.

28. A method according to claim 27, further comprising sensing the concentration of individual components present in the concentration pulse provided by one or more of the N interactive elements of each channel.

29. A method for concentrating one or more constituents of a fluid that is flowing through each channel of a plurality of channels, each channel having an interactive substance provided therein, the interactive substance adsorbing and desorbing selected constituents of the fluid depending on the temperature of the interactive substance, the interactive substance having an upstream portion and a downstream portion, the method comprising:

waiting for the interactive substance of each channel of the plurality of channels to adsorb one or more constituents from the fluid;

heating the upstream portion of the interactive substance, causing the upstream portion to desorb selected constituents into the fluid to produce a first concentration pulse in the respective channel, the first concentration pulse is carried by the fluid downstream toward the downstream portion of the interactive substance; and heating the downstream portion of the interactive substance when the first concentration pulse of the respective channel reaches the downstream portion, causing the downstream portion of the interactive substance to desorb selected constituents into the fluid and at least partially overlap the first concentration pulse to produce a second concentration pulse in the respective channel that is carried by the fluid downstream.

30. A concentrator for concentrating one or more constituents of a fluid, comprising:

a plurality of channels wherein each channel of said plurality has two or more interactive elements spaced along and exposed to the fluid, each of the interactive elements include an interactive substance that adsorbs and desorbs selected constituents of the fluid depending on the temperature of the interactive element, wherein at least two of the interactive elements are disposed within the fluid such that the sample fluid must pass by a first interactive element and then a second interactive element;

a plurality of heater elements, each heater element in thermal communication with a corresponding interactive element in each channel; and a controller coupled to the plurality of heater elements for allowing the two or more interactive elements of each channel to become exposed to the fluid before energizing the heater elements in a time phased sequence.

* * * * *